United States Patent [19]

Okano et al.

[11] 4,165,441
[45] Aug. 21, 1979

[54] PROCESS FOR THE PREPARATION OF STYRENE

[75] Inventors: Takeshi Okano; Tetsuo Masuyama, both of Machida; Toshiharu Yokoyama, Yokohama, all of Japan

[73] Assignee: Mitsubishi Chemical Industries, Ltd., Tokyo, Japan

[21] Appl. No.: 908,817

[22] Filed: May 23, 1978

[30] Foreign Application Priority Data

Jun. 6, 1977 [JP] Japan ............................. 52-66507
Aug. 23, 1977 [JP] Japan ............................. 52-100888
Nov. 8, 1977 [JP] Japan ............................. 52-133686
Nov. 17, 1977 [JP] Japan ............................. 52-138228

[51] Int. Cl.² ............................................. C07C 5/38
[52] U.S. Cl. ................................................. 585/444
[58] Field of Search ........................ 260/669 R, 680 E

[56] References Cited

U.S. PATENT DOCUMENTS

| | | | |
|---|---|---|---|
| 3,258,432 | 6/1966 | Gasson et al. | 260/680 E |
| 3,308,183 | 3/1967 | Bajars | 260/669 R |
| 3,308,185 | 3/1967 | Bajars | 260/669 R |
| 3,308,195 | 3/1967 | Bajars | 260/669 R |
| 3,328,478 | 6/1967 | Barclay et al. | 260/680 E |
| 3,346,513 | 10/1967 | Hadley | 260/680 E |
| 3,370,103 | 2/1968 | Callahan et al. | 260/680 E |
| 3,502,736 | 3/1970 | Sato et al. | 260/669 R |
| 3,792,103 | 2/1974 | Walker | 260/680 E |
| 3,845,156 | 10/1974 | Farha | 260/680 E |
| 4,036,901 | 7/1977 | Kawakami et al. | 260/669 R |

FOREIGN PATENT DOCUMENTS

42/8367 4/1967 Japan .
45/9168 4/1970 Japan .
45/9372 4/1970 Japan .
51/133236 11/1976 Japan .

*Primary Examiner*—C. Davis
*Attorney, Agent, or Firm*—Lane, Aitken & Ziems

[57] ABSTRACT

A process for producing styrene from 4-vinylcyclohexene by contacting it with molecular oxygen in a gaseous phase and at an elevated temperature in the presence of a catalyst which contains tin, antimony and oxygen.

15 Claims, No Drawings

PROCESS FOR THE PREPARATION OF STYRENE

BACKGROUND OF THE INVENTION

(1) Field of the Invention

This invention relates to a process for preparing styrene by oxidative dehydrogenation of 4-vinylcyclohexene in a gaseous phase in the presence of a novel catalyst. More particularly, the invention relates to a process for preparing styrene by oxidative dehydrogenation of 4-vinylcyclohexene by contacting it with oxygen or an oxygen-containing gas in a gaseous phase in the presence of a catalyst which is essentially composed of tin, antimony and oxygen.

(2) Description of the Prior Art

It is known that styrene is produced by oxidative dehydrogenation of 4-vinylcyclohexene in the presence of a catalyst. As the catalysts used for this reaction, there have been proposed the following for instance: palladium oxide catalysts (U.S. Pat. No. 3,502,736), supported palladium catalysts (Japanese Pat. Laid-Open No. 133236/76), platinum metal catalysts (Japanese Pat. Pub. No. 8367/67), molybdenum-bismuth-oxygen catalysts (Japanese Pat. Laid-Open No. 52139/76) and catalysts containing oxides of at least one metal selected from copper, zinc, arsenic, antimony, chromium, iron and cobalt (Japanese Pat. Pub. No. 9168/70).

The present inventors have pursued further researches for a catalyst more effective for the oxidative dehydrogenation of 4-vinylcyclohexene and found out as a result that a catalyst comprising as essential constituents tin, antimony and oxygen shows high activity and selectivity in the preparation of styrene from 4-vinylcyclohexene and is capable of producing styrene in a high yield. This invention was attained on the basis of such finding.

SUMMARY OF THE INVENTION

An object of this invention is to provide a process which is capable of producing styrene in a high yield.

Another object of this invention is to provide a styrene preparation process which can minimize the formation of the by-products such as ethylbenzene, benzene, oxygen-containing compounds, etc.

Still another object of this invention is to provide a styrene preparation process which can control the formation of carbon monoxide and carbon dioxide by combustion of the material and the product.

In the most broad sense, this invention is intended to provide a process for the preparation of styrene from 4-vinylcyclohexene by contacting it with molecular oxygen in a gaseous phase and at an elevated temperature in the presence of a catalyst which is essentially composed of tin, antimony and oxygen.

DETAILED DESCRIPTION OF THE INVENTION

The catalyst used in this invention (hereinafter referred to as "catalyst of this invention") is the one which contains tin, antimony and oxygen as essential constituents. Of these essential constituents, the tin component may be provided from tin oxides such as stannous oxide, stannic oxide, etc., hydrolyzed products of stannous chloride, stannic chloride, etc., or pyrolyzed products of organic tin compounds such as tin oxalate, tin acetate, etc. The organic tins, as shown in the Examples, may be dissolved in an inorganic acid such as hydrochloric acid and then neutralized with an alkali such as ammonia water. It is also possible to use the products obtained by oxidizing tin metals with nitric acid.

The antimony component may be provided from various sources, for example antimony oxides such as antimony trioxide, antimony tetroxide, antimony pentoxide, etc., hydrous antimony oxides, substances such as metaantimonic acid, orthoantimonic acid, pyroantimonic acid, etc., which are ultimately rendered into stable compounds such as antimony oxides by a chemical treatment or other treatments such as calcination, easily hydrolyzable antimony salts, for example, antimony halides such as antimony trichloride, antimony pentachloride, etc., and the products obtained by oxidizing antimony metals with nitric acid.

The catalyst performance can be further elevated by adding an adjunct as the fourth component in addition to the above-said essential constituents, that is, tin, antimony and oxygen. Preferred examples of such fourth component are tellurium, iron, zinc, copper, cobalt and the like.

In case of preparing a catalyst containing tellurium as the fourth component in addition to the three essential ingredients, such tellurium component may be provided from tellurium oxides such as tellurium dioxide, tellurium trioxide, etc. It is also possible to use telluric acid, tellurous acid, or metallic tellurium powder. Metallic tellurium may be oxidized with nitric acid.

Likewise, for preparing a catalyst containing iron as the fourth component, it is possible to use as iron component an iron oxide such as ferrous oxide, ferric oxide or tri-iron tetroxide in combination with the afore-said tin and antimony components. It is also possible to use the iron oxides produced by directly calcining the inorganic iron salts such as iron nitrate, iron chloride, etc., or organic iron salts such as iron acetate, iron oxalate, etc., or by calcining such iron salts after neutralizing them with an alkali such as ammonia water to form iron hydroxide. One may also use iron hydroxide or metallic iron. Metallic iron may be added in the form of fine powder or may be treated with heated nitric acid.

When using as the fourth component at least one metal selected from the group consisting of zinc, copper and cobalt for preparing the catalyst of this invention in combination with said three essential constituents, it is suggested to use, as the zinc component, zinc oxide or directly pyrolyzed products of inorganic salts of zinc nitrate, zinc carbonate, etc., or zinc oxides produced by hydrolyzing said salts with an alkali and then calcining them. Organic zinc such as zinc acetate may well be used.

As the copper component, one may use copper oxide such as cuprous oxide, cupric oxide, etc., directly pyrolyzed products of inorganic salts of copper nitrate, copper carbonate, etc., or copper oxides produced by hydrolyzing such salts with an alkali and then calcining them. Organic copper such as copper acetate may be also used.

The cobalt component may be provided from cobalt oxides such as cobalt dioxide, cobalt trioxide, etc. It is also possible to use directly pyrolyzed products of inorganic salts of cobalt nitrate, cobalt carbonate, etc., or cobalt oxides produced by hydrolyzing such salts with an alkali and then calcining them. Organic cobalt such as cobalt acetate may well be used.

If desired, other components than the above may also be added.

It is essential for the catalyst of this invention that all of said ingredients are mixed intimately and integrally with each other, and any known catalyst preparation method such as the mastecation method, evaporation-to-dryness method, immersion method, co-precipitation method or deposition method may be used for the preparation of the catalyst of this invention.

Although the thus prepared catalyst may be immediately put to use, it is recommended to subject the catalyst to a calcination treatment to further enhance the catalyst activity.

Such calcination treatment can be accomplished by heating the prepared catalyst composition with an oxygen-loaded gas at a temperature of from 200° to 1000° C., preferably from 600° to 1000° C., for the period of 1 to 24 hours.

Such calcination treatment on the prepared catalyst might cause scattering of the ingredients during the operation, so that when such treatment is performed, care should be taken to the material blending such that the respective ingredients would exist at the desired proportions after the calcination treatment.

The catalyst of this invention has the hereinbelow specified ranges of atomic ratio of the ingredients. When the catalyst is composed of tin, antimony and oxygen, the tin (Sn):antimony (Sb) atomic ratio is preferably 1:0.01–10, more preferably 1:0.05–5, most preferably 1:0.1–5. When the catalyst contains tellurium (Te) as the fourth component in addition to tin, antimony and oxygen, the Sn:Sb:Te atomic ratio is preferably 1:0.01–10:0.001–0.5, more preferably 1:0.05–5:0.01–0.1, most preferably 1:0.2–5:0.01–0.1, and when iron is contained as the fourth component, the tin, antimony and iron (Fe) atomic ratio in the catalyst is preferably Sn:Sb:Fe=1:0.01–10:0.001–5, more preferably 1:0.05–5:0.01–1, most preferably 1:0.2–5:0.01–1. In case zinc (Zn), copper (Cu) and/or cobalt (Co) are/is contained as the fourth component, the recommended range of atomic ratio of Sn:Sb:sum of Zn, Cu and/or Co is 1:0.01–10:0.01–0.5, more preferably 1:0.1–10:0.01–0.5.

The catalyst of this invention demonstrates excellent activity with no carrier, but it may be combined with a suitable carrier. Recommendable materials for use as carrier in the catalyst of this invention are silica, alumina, silicon carbide, alundum, silica-alumina, inorganic silicate and the like.

Other material such as caking agent capable of further improving the physical properties of the catalyst may be added, provided that addition of such material gives no adverse effect to the catalyst activity.

As regards the form of the catalyst of this invention, it may be shaped into the form of pellets convenient for use in the fixed bed reactions or may be shaped into granules to be used for the fluidized bed reactions.

Now the mode and the reaction conditions of the process of this invention are discussed.

The process can be carried out in any known manner used for gaseous phase reactions and the catalyst can be used either as a fixed bed, a fluidized bed or a moving bed.

The reaction temperature recommended to use in the process of this invention is usually 250° to 600° C., preferably 300° to 500° C. Although the reaction is generally performed under normal pressure, it may well be practiced under application of a low degree of pressure or under reduced pressure.

The gas hourly space velocity (GHSV) is an important reaction condition in a gaseous phase contact reaction using a solid catalyst. In case of using the catalyst of this invention, good results are obtained when said space velocity is on the order of 10,000 to 100 hr$^{-1}$, preferably 5,000 to 1,000 hr$^{-1}$. The "gas hourly space velocity" (GHSV) is the value of the volume of gas (reduced to NTP basis) which passes per hour per unit volume of the catalyst.

The starting material 4-vinylcyclohexene used in this invention needn't be high in purity, and it may contain other cyclic or chain hydrocarbons. Although air is usually used for the economical reason as the gas containing molecular oxygen in the process of this invention, it is of course possible to use air enriched suitably with oxygen. Oxygen is used in an amount of 0.7 to 10 times, preferably 1 to 4 times the molar quantity of 4-vinylcyclohexene. In addition to said 4-vinylcyclohexene and oxygen, it is also possible in this invention to use as diluent gas a gas which is essentially inert to the reaction of this invention, such as for example nitrogen gas, carbon dioxide gas or water vapor. Such diluent gas is preferably used in an amount of more than 0.5 times the molar quantity of 4-vinylcyclohexene. Feed of the material 4-vinylcyclohexene for the reaction of this invention must be conducted with the greatest circumspection because this material is highly reactive. 4-vinylcyclohexene is supplied into the reactor after vaporized by an evaporator or other means, but since it might induce a side reaction with oxygen under the reaction conditions of this invention even in the absence of a catalyst or in the presence of an inert base such as granular quartz, it is recommended to mix said material with the oxygen source gas just before the catalyst layer. It is also desirable to quickly cool the outlet of the catalyst layer because otherwise the starting material 4-vinylcyclohexene and the object product styrene are apt to be polymerized.

According to the process of this invention, it is possible to produce styrene at high conversion and selectivity. Also, since evolution of heat due to combustion is suppressed owing to high selectivity of styrene, the required amount of diluent gas is minimized and a high-concentration reactant gas can be used. The limited amount of carbon deposition in the reaction is another merit of the process of this invention for advantageous industrial production of styrene.

The invention is now described in further detail by way of the examples, but these examples should not be construed as limiting the scope of the invention. In the following examples, the conversion of 4-vinylcyclohexene and selectivities of styrene, ethylbenzene, benzene, carbon oxides and deposited carbon were determined from the following formulae:

$$\text{Conversion (\%) of 4-vinylcyclohexene} = \frac{\text{Number of moles of consumed 4-vinylcyclohexene}}{\text{Number of moles of supplied 4-vinylcyclohexene}} \times 100$$

$$\text{Selectivity (\%) of styrene} = \frac{\text{Number of moles of produced styrene}}{\text{Number of moles of consumed 4-vinylcyclohexene}} \times 100$$

$$\text{Selectivity (\%) of ethylbenzene} = \frac{\text{Number of moles of produced ethylbenzene}}{\text{Number of moles of consumed 4-vinylcyclohexene}} \times 100$$

Selectivity (%) of benzene =

$$\text{Selectivity (\%) of benzene} = \frac{[\text{Number of moles of produced benzene}] \times 6/8}{\text{Number of moles of consumed 4-vinylcyclohexene}} \times 100$$

$$\text{Selectivity (\%) of carbon oxides} = \frac{[\text{Number of moles of produced CO and CO}_2] \times 1/8}{\text{Number of moles of consumed 4-vinylcyclohexene}} \times 100$$

$$\text{Selectivity (\%) of deposited carbon} = \frac{\text{Number of moles of produced carbon}] \times 1/8}{\text{number of moles of consumed 4-vinylcyclohexene}} \times 100$$

The number of moles of produced carbon was measured in the following way. (i) After the reaction, the catalyst layer is purged with nitrogen gas. (ii) Air or oxygen gas is passed through the catalyst layer heated to 500° C. (iii) Upon combustion, carbon is turned into carbon monoxide and carbon dioxide, but carbon monoxide is made into carbon dioxide with heated copper oxide and the whole carbon dioxide is adsorbed in the commercially available caustic soda granules for analysis. (iv) The total adsorption (weight) is measured.

The number of moles of carbon is calculated from the following formula:

Number of moles of carbon = Total weight of adsorption/44

The catalyst activity test in Examples 1-5 was conducted in the following way. 5 ml of the catalyst regulated to 7- to 10-mesh particle size was charged into a glass made reactor with inner diameter of 19 mm, and after further loading SUS 304 filler in front and rear parts of the catalyst layer, the reactor was heated in an electric furnace. Then the gas of the following composition was passed into the reactor at GHSV = 1,240 hr$^{-1}$ [LHSV (liquid hourly space velocity of 4-vinylcyclohexene) = 0.5 hr$^{-1}$] and under normal reaction pressure. 4-vinylcyclohexene/O$_2$/N$_2$/water vapor = 7/10.5/22.9/59.6 (molar ratio). Then, the reaction mixture gas which has flowed out from the reactor outlet after the completion of the reaction was cooled by adding cooling water continuously at the rate of 1 l/hr, and the liquefied reaction mixture gas was collected by a collector. The liquid material in the collector remained separated into the water layer and oil layer, so the oil layer accumulated in the collector during the predetermined period of time was analyzed by gas chromatograph to determine the product.

The reaction mixture gas component non-liquefied by said cooling treatment was collected by a gas sampler and subjected to a gas chromatographic quantitative analysis.

The continuously added cooling water was drawn out steadily from the bottom of the collector.

In Examples 6-23, the reaction was carried out similarly to Example 1, and the reaction mixture gas effused out from the reactor after the reaction was guided into the ice-cooled collector, liquefied there and then collected. The oil layer accumulate in the collector during the predetermined period of time was analyzed by gas chromatography to determine the product. The reaction mixture gas non-liquefied by said treatment was collected by a gas sampler and analyzed by gas chromatograph for quantitative determination.

EXAMPLE 1

18.37 gr of tin oxalate (reagent grade) was dissolved in 400 ml of 4 N hydrochloric acid, and to this aqueous solution was added 30.69 gr of antimony tri-oxide [reagent grade (95% product)] under agitation. Then 145 ml of ammonia water [reagent grade (28% product)] was added dropwise. There was ultimately produced a yellow precipitate. Then this precipitate was washed with 5 liters of ion exchange water and fractionated by filtration. The cake was dried at 110° C. for 10 hours and then calcined at 500° C. for 3 hours and then at 900° C. for additional 2 hours. The resultant product was shaped and regulated in particle size to form a catalyst for reaction. The metal composition in this catalyst was: Sn:Sb = 1:2.5 (by atomic ratio). The activity test of this catalyst was carried out in the manner described above at reaction temperature of 400° C. The results as obtained after three-hour reaction are shown in Table 1 below.

EXAMPLES 2-4

Catalysts were prepared in the same way as Example 1 but by changing the compositional ratio of tin and antimony, and the reactions were performed by using these catalysts under the same reaction conditions as used in Example 1. The results obtained after three hours of reaction are shown in Table 1 below.

Table 1

| Example No. | Catalyst composition Sn/Sb (atomic ratio) | 4-vinylcyclohexene conversion (%) | Selectivity (%) | | | | |
|---|---|---|---|---|---|---|---|
| | | | Styrene | Ethylbenzene | Benzene | Carbon oxides | Deposited carbon |
| 1 | 1/2.5 | 67.1 | 67.9 | 4.1 | 0.3 | 2.1 | 0.10 |
| 2 | 1/0.5 | 82.4 | 58.9 | 6.0 | 0.2 | 2.4 | 0.07 |
| 3 | 1/1.0 | 77.7 | 61.5 | 3.5 | 0.3 | 2.6 | 0.13 |
| 4 | 1/5.0 | 37.2 | 59.3 | 3.8 | 0.3 | 1.3 | — |

EXAMPLES 5-1-5-3

The catalysts prepared after the manner of Example 1 were subjected to an activity test carried out in the same way as described above at the reaction temperatures of 410° C., 450° C. and 475° C., respectively. The results obtained after this 3-hour test are shown in Table 2 below.

Table 2

| Example No. | Reaction temperature °C. | 4-vinylcyclohexene conversion (%) | Selectivity (%) | | | |
|---|---|---|---|---|---|---|
| | | | Styrene | Ethylbenzene | Benzene | Carbon oxides |
| 5-1 | 410 | 62.7 | 60.5 | 2.3 | 0.2 | 2.6 |
| 5-2 | 450 | 82.3 | 59.5 | 1.9 | 0.6 | 4.0 |
| 5-3 | 475 | 83.9 | 59.1 | 1.6 | 0.7 | 4.9 |

EXAMPLE 6

The above-described activity test was carried out at reaction temperature of 400° C. on the catalyst of the same composition as that of Example 2, and the results as obtained three hours there-after are shown in Table 3 below.

EXAMPLE 7

An activity test was carried out under the same reaction conditions as Example 6 on the catalyst same in composition as that of Example 3. The results obtained after three-hour reaction are shown in Table 3 below.

Table 3

| Example No. | Catalyst composition Sn/Sb (atomic ratio) | 4-vinylcyclohexene conversion (%) | Selectivity (%) | | | | |
|---|---|---|---|---|---|---|---|
| | | | Styrene | Ethylbenzene | Benzene | Carbon oxides | deposited carbon |
| 6 | 1/0.5 | 83.7 | 72.0 | 7.4 | 0.5 | 3.3 | 0.07 |
| 7 | 1/1 | 69.6 | 71.3 | 4.2 | 0.6 | 2.7 | 0.14 |

EXAMPLE 8

1.66 gr of metallic antimony powder (purity: 99.9%; particle size: less than 100 meshes) was added portionwise into 50 ml of heated nitric acid (specific gravity: 1.38), and after evolution of brown gas has ceased, 60 ml of nitric acid (specific gravity: 1.38) was added, followed by portionwise addition of 20.20 gr of metallic tin powder (purity: 99.9%, particle size: less than 100 meshes), and after cease of evolution of brown gas, the mixture was allowed to stand for several hours. Then excess nitric acid was decanted and the precipitate was washed twice with 300 ml of water and then heated under agitation to evaporate to dryness. The product was then calcined by passing air at 500° C. for 3 hours, and after shaping and size regulation, the product was further calcined by passing air at 900° C. for 2 hours to obtain a reaction catalyst. This catalyst had the metallic composition of Sn:Sb=1:0.08 (by atomic ratio).

This catalyst was subjected to an activity test same as practiced in Example 6 except for use of an SUS 304 made reactor at the reaction temperature of 380° C. The results obtained 2 hours later are shown in Table 4.

EXAMPLE 9

A catalyst with the metallic composition of Sn:Sb=1:0.05 (by atomic ratio) was prepared according to the process of Example 8 and subjected to an activity test according to the method of Example 8 at the reaction temperature of 360° C. The results obtained 2 hours later are shown in Table 4.

EXAMPLE 10

A catalyst with the metallic composition of Sn:Sb=1:0.1 (by atomic ratio) was prepared according to the process of Example 8 and subjected to the same activity test as practiced in Example 8 at the reaction temperature of 400° C. The results obtained after 2-hour reaction are shown in Table 4 below.

Table 4

| Example No. | Catalyst composition | | Reaction temperature (°C.) | 4-vinylcyclohexene conversion (%) | Selectivity (%) | | | |
|---|---|---|---|---|---|---|---|---|
| | Sn | Sb | | | Styrene | Ethylbenzene | Benzene | Carbon oxides |
| 8 | 1 | 0.08 | 380 | 91.7 | 87.5 | 1.4 | 0.6 | 3.0 |
| 9 | 1 | 0.05 | 360 | 79.9 | 88.2 | 1.4 | 0.2 | 2.7 |
| 10 | 1 | 0.1 | 400 | 94.4 | 84.0 | 1.1 | 1.7 | 4.5 |

EXAMPLE 11

2.44 gr of metallic antimony powder (purity: 99.9%, particle size: less than 100 meshes) was added portionwise into 43 ml of heated nitric acid (specific gravity: 1.38), and after evolution of brown gas has ceased, 30 ml of nitric acid (specific gravity: 1.38) was added, followed by portionwise addition of 11.88 gr of metallic tin powder (purity: 99.9%, particle size: less than 100 meshes), and after cease of evolution of brown gas, the mixture was allowed to stand for several hours. Excess nitric acid was decanted and the precipitate was washed twice with 300 ml of water, added with 60.48 gr of carrier component silica sol ($SiO_2$ content: 20 wt%) and then heated under sufficient agitation and thereby evaporated to dryness. The resultant product was calcined by passing air at 500° C. for 3 hours, and after shaping and particle size regulation, it was further calcined by passing air at 900° C. for 2 hours to obtain a catalyst preparation for the reaction of this invention. This catalyst preparation had the metallic composition of Sn:Sb:Si=1:0.2:2.01 (by atomic ratio). An activity test was carried out on this catalyst preparation according to the method of Example 8 at the reaction temperature of 420° C. The results as obtained 2 hours after start of the test are shown in Table 5.

EXAMPLE 12

A catalyst was prepared in the same way as Example 11 except that calcination was performed at 940° C. for 2 hours, and this catalyst was subjected to the activity test of Example 8 at reaction temperature of 420° C.

The results 2 hours later are shown in Table 5.

Table 5

| Example No. | Catalyst composition Sn | Sb | Si | Final calcination temperature (°C.) | Reaction temperature (°C.) | 4-vinyl-cyclohexene conversion (%) | Styrene | Selectivity (%) Ethyl-benzene | Benzene | Carbon oxides |
|---|---|---|---|---|---|---|---|---|---|---|
| 11 | 1 | 0.2 | 2.01 | 900 | 420 | 88.1 | 76.0 | 6.1 | 1.5 | 5.0 |
| 12 | 1 | 0.2 | 2.01 | 940 | 420 | 85.2 | 81.7 | 3.8 | 1.0 | 3.1 |

EXAMPLE 13

27.56 gr of tin oxalate (reagent grade) was dissolved in 450 ml of 4 N hydrochloric acid, and to this aqueous solution was added 9.21 gr of antimony trioxide (reagent grade) under agitation to prepare a homogeneous aqueous solution. Then 174 ml of ammonia water [reagent grade (28% product)] was added portionwise into said solution, and there was ultimately formed a yellow precipitate. This precipitate was washed four times with 3 liters of ion exchange water and then added with 20 ml aqueous solution of 0.556 gr of telluric acid (reagent grade). This mixture was agitated and evaporated to dryness over an electric heater, followed by 3-hour calcination at 500° C. and additional 2-hour calcination at 900° C. The resultant product was shaped and regulated in particle size to prepare a catalyst for use in the reaction of this invention. This catalyst had the metallic composition of Sn:Sb:Te=1:0.5:0.02 (by atomic ratio). This catalyst was then subjected to an activity test according to the above-described method. The results obtained after 2-hour reaction at various temperatures are shown in Table 6.

EXAMPLES 14-15

Catalysts were prepared in the same way as Example 13 except for change of the tellurium composition, and these catalysts were reacted under the reaction conditions of Example 13. The results obtained after 2-hour reaction at various temperatures are shown in Table 6.

Table 6

| Example No. | Catalyst composition Sn/Sb/Te (atomic ratio) | Reaction temperature (°C.) | 4-vinylcyclohexene conversion (%) | Styrene | Selectivity (%) Ethyl-benzene | Benzene | Carbon oxides |
|---|---|---|---|---|---|---|---|
| 13 | 1:0.5:0.02 | 400 | 81.3 | 78.6 | 5.7 | 1.0 | 2.4 |
|  |  | 415 | 81.0 | 81.0 | 3.6 | 1.1 | 3.3 |
| 14 | 1:0.5:0.01 | 400 | 85.1 | 70.7 | 11.3 | 0.8 | 3.1 |
|  |  | 420 | 80.8 | 78.8 | 5.3 | 1.4 | 4.0 |
| 15 | 1:0.5:0.05 | 400 | 66.9 | 71.0 | 0.9 | 0.4 | 2.6 |
|  |  | 420 | 75.6 | 71.2 | 0.9 | 0.8 | 4.7 |
|  |  | 440 | 81.3 | 70.9 | 0.9 | 1.3 | 4.8 |

EXAMPLE 16

13.78 gr of tin oxalate (reagent grade) was dissolved in 550 ml of 4 N hydrochloric acid, and to this solution was added 23.02 gr of antimony trioxide (reagent grade) under agitation to obtain a homogeneous solution. Then 194 ml of ammonia water [reagent grade (28% product)] was added dropwise to finally form a yellow precipitate. The solution pH at that time was 8.6. The precipitate was washed four times with 3 liters of ion exchange water and then added with 20 ml aqueous solution of 2.45 gr of iron nitrate (reagent grade), and the mixture was evaporated under agitation to dryness over an electric heater. The product was then calcined by passing air at 500° C. for 3 hours, and after shaping and size regulation, the product was further calcined by passing air at 900° C. for 2 hours. The thus obtained product was used as the catalyst for the reaction of this invention. The metallic composition in this catalyst was: Sn:Sb:Fe=1:2.5:0.1 (atomic ratio). This catalyst was then subjected to an activity test according to the above-described method. The results as obtained after 2-hour reaction at various temperatures are shown in Table 7.

EXAMPLES 17-19

Catalysts were prepared after the manner of Example 16 but by changing the iron composition, and these catalysts were reacted under the reaction conditions of Example 16. The results obtained after 2-hour reaction at various temperatures are shown in Table 7 below.

Table 7

| Example No. | Catalyst composition Sn/Sb/Fe (atomic ratio) | Reaction temperature (°C.) | 4-vinylcyclohexene conversion (%) | Styrene | Selectivity (%) Ethyl-benzene | Benzene | carbon oxides |
|---|---|---|---|---|---|---|---|
|  |  | 400 | 62.1 | 81.3 | 3.0 | 0.6 | 3.6 |
| 16 | 1:2.5:0.1 | 420 | 70.6 | 81.6 | 2.2 | 0.9 | 7.7 |
|  |  | 440 | 74.8 | 82.4 | 1.7 | 1.3 | 8.1 |
|  |  | 400 | 67.1 | 78.2 | 4.9 | 0.6 | 5.2 |
| 17 | 1:2.5:0.3 | 420 | 69.7 | 80.7 | 2.4 | 0.9 | 7.0 |
|  |  | 440 | 71.4 | 80.8 | 1.9 | 1.2 | 7.8 |
|  |  | 400 | 68.2 | 79.4 | 5.7 | 0.8 | 3.3 |
| 18 | 1:2.5:0.5 | 420 | 72.9 | 81.2 | 2.7 | 1.2 | 6.7 |

Table 7-continued

| Example No. | Catalyst composition Sn/Sb/Fe (atomic ratio) | Reaction temperature (°C.) | 4-vinylcyclohexene conversion (%) | Selectivity (%) | | | |
|---|---|---|---|---|---|---|---|
| | | | | Styrene | Ethylbenzene | Benzene | carbon oxides |
| | | 440 | 74.4 | 81.1 | 1.8 | 1.5 | 7.3 |
| | | 400 | 60.9 | 80.7 | 3.5 | 0.9 | 4.0 |
| 19 | 1:2.5:1 | 420 | 65.5 | 78.3 | 1.9 | 1.3 | 4.9 |
| | | 440 | 70.0 | 78.7 | 1.7 | 1.6 | 6.4 |

EXAMPLE 20

27.56 gr of tin oxalate (reagent grade) was dissolved in 450 ml of 4 N hydrochloric acid, and to this solution was added 9.21 gr of antimony trioxide (reagent grade) to form a homogeneous solution. Then 174 ml of ammonia water [reagent grade (28% product)] was added portionwise to ultimately form a yellow precipitate. The precipitate was washed four times with 3 liters of ion exchange water and then added with 20 ml aqueous solution of 1.80 gr of zinc nitrate (reagent grade), and the mixture was evaporated to dryness under agitation over an electric heater. The obtained powdery product was calcined in an electric furnace by passing air at 500° C. for 3 hours, followed by shaping and particle size regulation, thereby preparing a catalyst for the reaction of this invention.

This catalyst had the metallic composition of Sn:Sb:Zn=1:0.5:0.05 (atomic ratio). An activity test was carried out on this catalyst according to the above-described test method. The results obtained after 2-hour reaction at various temperatures are shown in Table 8.

EXAMPLE 21

A catalyst was prepared in the same way as Example 20 except that calcination in an electric furnace was performed by passing air at 1,000° C. for 2 hours after 3-hour and 500° C. calcination, shaping and particle size regulation according to the method of Example 20, and this catalyst was subjected to an activity test according to the above-described method. The results obtained after 2-hour reaction at various temperatures are shown in Table 8.

EXAMPLE 22

There was prepared a catalyst by following the same procedure as Example 21 except for use of 20 ml aqueous solution of 1.46 gr of copper nitrate (reagent grade) instead of the aqueous solution of zinc nitrate. This catalyst had the metallic composition of Sn:Sb:Cu=1:0.5:0.05 (by atomic ratio). The activity of this catalyst was tested according to the method used in the preceding examples. The results obtained after 2-hour reaction test at various temperatures are shown in Table 8.

EXAMPLE 23

A catalyst was prepared in the same way as Example 21 except for addition of 20 ml aqueous solution of 1.78 gr of cobalt nitrate (reagent grade) instead of the aqueous solution of zinc nitrate and final calcination of 2-hour at 900° C. instead of 2-hour at 1000° C. The metallic composition in this catalyst was: Sn:Sb:Co=1:0.5:0.05. The activity of this catalyst was tested by the above-described method. The results obtained after 2-hour reaction at various temperatures are shown in Table 8.

Table 5

| Example No. | Catalyst composition (atomic ratio) | Final calcination temperature (°C.) | Reaction temperature (°C.) | 4-vinyl-cyclohexene conversion (%) | Selectivity (%) | | | |
|---|---|---|---|---|---|---|---|---|
| | | | | | Styrene | Ethylbenzene | Benzene | Carbon oxides |
| 20 | Sn/Sb/Zn | | 380 | 50.5 | 82.2 | 1.3 | 0.6 | 3.4 |
| | (1/0.5/0.05) | 500 | 400 | 59.8 | 79.7 | 1.1 | 0.8 | 4.0 |
| 21 | Sn/Sb/Zn | | 400 | 65.7 | 81.7 | 6.6 | 0.4 | 2.0 |
| | (1/0.5/0.05) | 1000 | 420 | 73.9 | 85.4 | 4.0 | 0.8 | 2.8 |
| | | | 440 | 77.3 | 81.3 | 2.5 | 1.1 | 3.4 |
| 22 | Sn/Sb/Cu | | 400 | 86.4 | 79.4 | 4.4 | 0.4 | 2.4 |
| | (1/0.5/0.05) | 1000 | 420 | 76.3 | 81.1 | 3.1 | 0.8 | 2.9 |
| | | | 440 | 78.8 | 80.3 | 2.1 | 1.2 | 3.7 |
| 23 | Sn/Sb/Co | | 420 | 70.3 | 80.5 | 1.8 | 1.1 | 4.8 |
| | (1/0.5/0.05) | 900 | 440 | 70.0 | 77.2 | 1.5 | 1.5 | 8.1 |

What is claimed is:

1. A process for producing styrene from 4-vinylcyclohexene by contacting it with molecular oxygen in a gaseous phase and at an elevated temperature in the presence of a catalyst which contains tin, antimony and oxygen.

2. The process according to claim 1, wherein the atomic ratio of tin (Sn) to antimony (Sb) in the catalyst (Sn:Sb) is 1:0.01-10.

3. The process according to claim 1, wherein said catalyst further contains tellurium.

4. The process according to claim 3, wherein the atomic ratio of tin to antimony to tellurium in the catalyst (Sn:Sb:Te) is 1:0.01-10:0.001-0.5.

5. The process according to claim 1, wherein said catalyst further contains iron.

6. The process according to claim 5, wherein the atomic ratio of tin to antimony to iron in the catalyst (Sn:Sb:Fe) is 1:0.01-10:0.001-5.

7. The process according to claim 1, wherein said catalyst further contains at least one metal selected from the group consisting of zinc, copper and cobalt.

8. The process according to claim 7, wherein the atomic ratio of tin to antimony to zinc, copper and/or cobalt (Sn:Sb:sum of Zn, Cu and/or Co) is 1:0.01–10:0.01–0.5.

9. The process according to any of claims 1, 2, 3, 4, 5, 6, 7 or 8, wherein the reaction temperature is from 250° to 600° C.

10. The process according to claim 1 wherein said catalyst is prepared by intimate mixing of the respective ingredients and subsequent calcination treatment.

11. The process according to claim 3 wherein said catalyst is prepared by intimate mixing of the respective ingredients and subsequent calcination.

12. The process according to claim 5 wherein said catalyst is prepared by intimate mixing of the respective ingredients and subsequent calcination.

13. The process according to claim 7 wherein said catalyst is prepared by intimate mixing of the respective ingredients and subsequent calcination.

14. The process according to claim 10, 11, 12 or 13 wherein the calcination treatment is performed at a temperature of from 200° to 1000° C.

15. The process according to claim 10, 11, 12 or 13 wherein said calcination treatment is performed at a temperature from 600° to 1000° C.